(12) United States Patent  (10) Patent No.: US 7,649,114 B2
Buschmann et al.  (45) Date of Patent: Jan. 19, 2010

(54) SEPARATION OF STEREOISOMERIC N,N-DIALKYLAMINO-2ALKYL-3-HYDROXY-3-PHENYLALKANES

(75) Inventors: Helmut Heinrich Buschmann, Sant just Desvern (ES); Wolfgang Hell, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/915,653

(22) PCT Filed: May 29, 2006

(86) PCT No.: PCT/EP2006/005101
§ 371 (c)(1),
(2), (4) Date: Jul. 3, 2008

(87) PCT Pub. No.: WO2006/125675
PCT Pub. Date: Nov. 30, 2006

(65) Prior Publication Data
US 2008/0269524 A1 Oct. 30, 2008

(30) Foreign Application Priority Data
May 27, 2005 (DE) .................. 10 2005 024 824
Jul. 15, 2005 (DE) .................. 10 2005 033 732

(51) Int. Cl.
*C07C 269/08* (2006.01)
*C07C 67/48* (2006.01)
*C07C 209/88* (2006.01)
(52) U.S. Cl. ................ 564/304; 560/135; 560/136; 560/142; 564/302
(58) Field of Classification Search ............... 560/135, 560/136, 142; 564/302, 304
See application file for complete search history.

(56) References Cited

U.S. PATENT DOCUMENTS
4,155,935 A 5/1979 Yardley et al.
(Continued)

FOREIGN PATENT DOCUMENTS
CH 415 602 1/1967
(Continued)

OTHER PUBLICATIONS
Juan R. Dehli et al., "Stereoselective alkylation-reduction of β-keto nitriles by the fungus *Curvularia lunata*", Tetrahedron: Asymmetry vol. 12 (2001) pp. 1485-1492.
(Continued)

*Primary Examiner*—Peter G O'Sullivan
(74) *Attorney, Agent, or Firm*—Crowell & Moring LLP

(57) ABSTRACT

The invention concerns a method for the isolation of a stereoisomer from a mixture comprising the two stereoisomers of the general formulae (I-A) and (I-A') and/or the two stereoisomers of the general formulae (I-B) and (I-B')

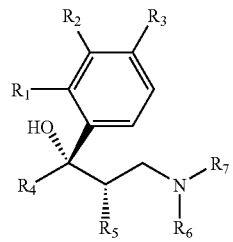

(I-A)

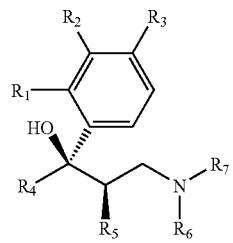

(I-A')

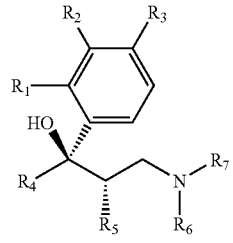

(I-B)

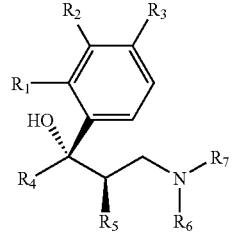

(I-B')

in which
$R_1$, $R_2$ and $R_3$, identical or different, are selected from the group consisting of —H, —F, —Cl, —$C_1$-$C_6$-alkyl, —S—$C_1$-$C_6$-alkyl, —OH, —O—$C_1$-$C_6$-alkyl, —O—$C_1$-$C_6$-alkylenephenyl, —OCO—$C_1$-$C_6$-alkyl, —OCON($C_1$-$C_6$-alkyl)$_2$ and —O—SiR$_8$R$_9$R$_{10}$ (in which $R_8$, $R_9$ and $R_{10}$, identical or different, are —$C_1$-$C_6$-alkyl or -phenyl);
$R_4$ is —H or —$C_1$-$C_6$-alkyl;
$R_5$ is —$C_1$-$C_6$-alkyl; and
$R_6$ and $R_7$, identical or different, are —H or —$C_1$-$C_6$-alkyl;
or their salts with organic or inorganic acids;
comprising the step
(a) manipulating the mixture ratio of the stereoisomers in the mixture so that at least one of the stereoisomers is present in an enantiomeric excess.

8 Claims, No Drawings

U.S. PATENT DOCUMENTS

| | | |
|---|---|---|
| 5,243,076 A | 9/1993 | Skidmore et al. |
| 6,248,737 B1 | 6/2001 | Buschmann et al. |

FOREIGN PATENT DOCUMENTS

| | | |
|---|---|---|
| DE | 124 521 | 3/1977 |
| DE | 195 47 766 A1 | 6/1997 |
| DE | 199 15 602 A1 | 10/2000 |
| DE | 101 08 308 A1 | 8/2002 |
| DE | 695 24 962 T2 | 10/2002 |
| EP | 0 176 049 B1 | 4/1986 |
| EP | 0 693 475 A1 | 1/1996 |
| EP | 0 780 369 A1 | 6/1997 |
| EP | 0 786 450 B1 | 7/1997 |
| EP | 0 693 475 B1 | 2/1998 |
| EP | 0 983 995 B1 | 3/2000 |
| EP | 1 246 790 B1 | 10/2002 |

OTHER PUBLICATIONS

L. Angiolini et al., "Stereochemistry of Mannich Bases-II Stereospecific Synthesis and Absolute Configuration of Diastereoisomeric 1-Phenyl-1,2-Dimethyl-3-Dimethylamino-Propan-1-OLS" Tetrahedron vol. 25., (1969), pp. 4211-4216.

German Search Report dated Mar. 2, 2006, including an English translation (Nine (9) pages).

International Search Report dated Sep. 8, 2006, including an English translation (Seven (7) pages).

Form PCT/ISA/220 and Form PCT/ISA/237 dated Sep. 8, 2006 (Seven (7) pages).

English translation of International Preliminary Report (Form PCT/IPEA/409) along with Form PCT/IB/338, including an English translation of the pertinent portions (Six (6) pages).

SEPARATION OF STEREOISOMERIC N,N-DIALKYLAMINO-2ALKYL-3-HYDROXY-3-PHENYLALKANES

The invention concerns a method for the separation of stereoisomeric N,N-dialkyl-amino-2-alkyl-3-hydroxy-3-phenylalkanes.

Opioids have been used for many years as analgesics for the treatment of pain although they can induce a number of side effects, for example addiction and dependency, respiratory depression, gastrointestinal inhibition and constipation. Over an extended period or at high doses they can only be administered with particular precautionary measures such as special prescribing requirements.

It is known that certain N,N-dialkylamino-2-alkyl-3-hydroxy-3-phenylalkanes (especially 1-phenyl-3-dimethylaminopropane compounds) possess analgesic activity without causing the side effects typical of opioids. These compounds are characterised by a pronounced analgesic action that is significantly increased in comparison with, for example, the opioid tramadol.

These analgesically active N,N-dialkylamino-2-alkyl-3-hydroxy-3-phenylalkanes are chiral. Since two chiral centres are usually present, the compounds exist in the form of 4 stereoisomers, i.e. two enantiomeric pairs that are diastereomeric with one another.

The activity of an analgesic is frequently attributable to its interaction with a certain receptor of a human or animal cell. Since these receptors are constructed of chiral amino acids and optionally also chiral glycosides, their interaction with chiral pharmaceuticals is stereoselective. Therefore the pharmacological activity of chiral pharmaceuticals is frequently different for the individual stereoisomers.

There is therefore a requirement for a method for the separation of the stereoisomers, i.e. the diastereoisomers and enantiomers, of N,N-dialkylamino-2-alkyl-3-hydroxy-3-phenylalkanes.

The synthesis of (2RS,3RS)-1-dimethylamino-3-(3-methoxyphenyl)-2-methylpentan-3-ol is known from of EP-A 693 475. The separation of the diastereoisomers, that is the two enantiomeric pairs, is carried out by hydrochloride precipitation with trimethylchlorosilane/water in 2-butanone. The racemic mixture of the two enantiomers of (2R,3R) and (2S,3S) configuration is carried out by separation on a chiral HPLC column.

However, the chromatographic separation of enantiomers on chiral stationary phases is usually unsuitable for relatively large quantities of active compounds and is instead used almost solely for analytical purposes. There is therefore a requirement for a method that is also suitable for the separation of the enantiomers of chiral N,N-dialkylamino-2-alkyl-3-hydroxy-3-phenylalkanes on a preparative scale.

Thus the problem that forms the basis of the invention is to provide a method for the separation of the stereoisomers, preferably enantiomers, of chiral N,N-dialkylamino-2-alkyl-3-hydroxy-3-phenylalkanes that can also be carried out on the gram and kilogram scale. The method must be cost-effective and guarantee a good yield and high enantiomeric purity.

This object is achieved by the subject matter of the claims. It has surprisingly been found that the isolation of a stereoisomer from a mixture comprising the two stereoisomers of the general formulae (I-A) and (I-A') and/or the two stereoisomers of the general formulae (I-B) and (I-B'),

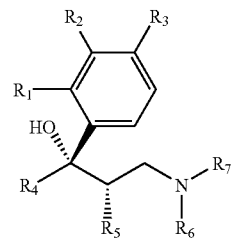
(I-A)

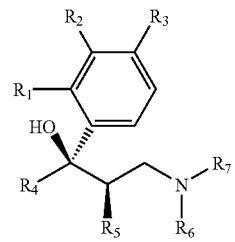
(I-A')

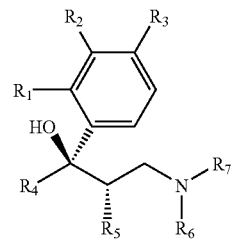
(I-B)

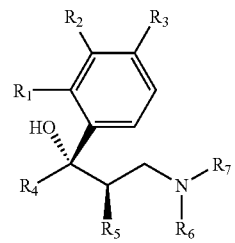
(I-B')

in which
$R_1$, $R_2$ and $R_3$, identical or different, are selected from the group consisting —H, —F, —Cl, —$C_1$-$C_6$-alkyl, —S—$C_1$-$C_6$-alkyl, —OH, —O—$C_1$-$C_6$-alkyl, —O—$C_1$-$C_6$-alkylenephenyl, —OCO—$C_1$-$C_6$-alkyl, —OCON($C_1$-$C_6$-alkyl)$_2$ and —O—$SiR_8R_9R_{10}$ (in which $R_8$, $R_9$ and $R_{10}$, identical or different, are —$C_1$-$C_6$-alkyl or -phenyl);
$R_4$ is —H or —$C_1$-$C_6$-alkyl;
$R_5$ is —$C_1$-$C_6$-alkyl; and
$R_6$ and $R_7$, identical or different, are —H or —$C_1$-$C_6$-alkyl; or their salts with organic or inorganic acids;

is possible by a method comprising the step
(a) manipulating the mixture ratio of the stereoisomers in the mixture so that at least one of the stereoisomers, preferably the stereoisomer to be isolated, is present in an enantiomeric excess.

It has surprisingly been found that individual stereoisomers may be crystallised with high stereoselectivity from the mixture of stereoisomers when at least one of the stereoisomers is not present in racemic mixture, but instead in an enantiomeric excess.

The compounds of the general formula (I) exhibit at least two chiral centres. The compounds can be synthesised in different ways. For example, it is possible firstly to prepare a Mannich base in a Mannich reaction by which means the first chiral centre is produced:

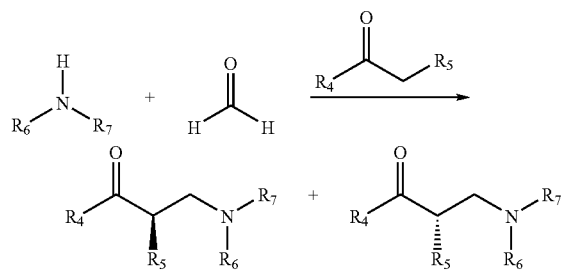

If the Mannich reaction takes place without chiral induction, i.e. in the absence of chiral auxiliaries, chiral catalysts, chiral solvents, etc., the Mannich base is formed as a racemic mixture, since transition states leading to the two enantiomeric Mannich bases are enantiomorphic and thus energetically identical.

The second chiral centre can be introduced, for example, by reaction of the Mannich base with a Grignard reagent at the carbonyl:

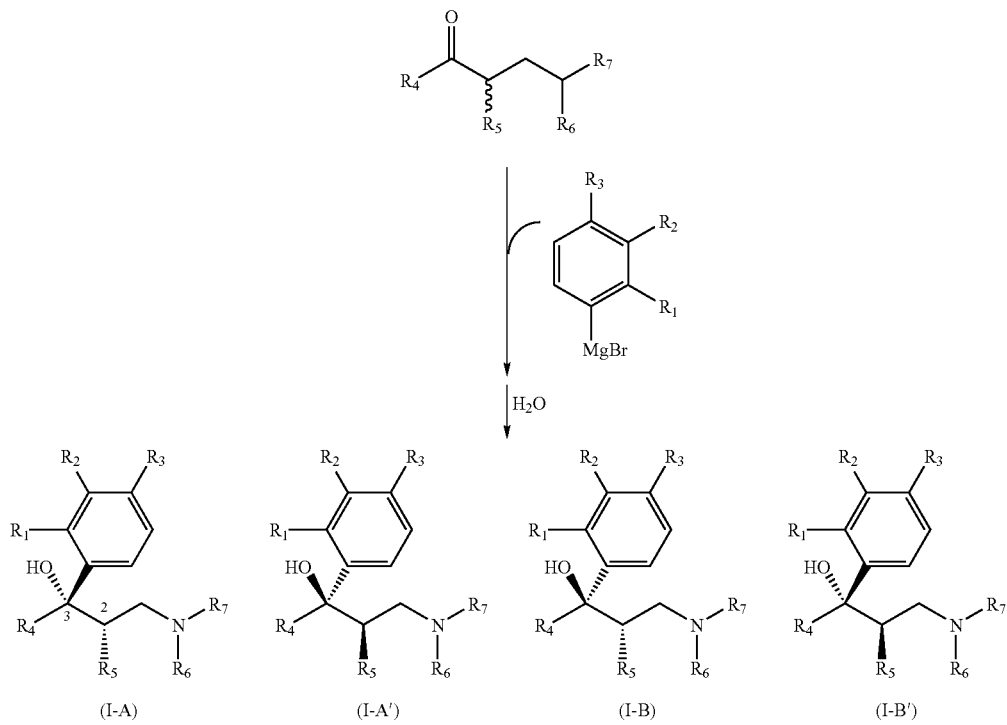

In this way, the four stereoisomeric N,N-dialkylamino-2-alkyl-3-hydroxy-3-phenyl-alkanes of the general formulae (I-A), (I-A'), (I-B) and (I-B') are formed from the racemic Mannich base. Depending on the substitution pattern at the two chiral centres, the R— or S-configuration is in each case formed.

In principal, it is also possible for further chiral centres also to be present in one of the side chains. In the case of three chiral centres, the number of stereoisomers increases to a total of eight, four enantiomeric pairs being present. The N,N-dialkyl-amino-2-alkyl-3-hydroxy-3-phenylalkanes preferably comprise only two chiral centres.

Preferably, the stereoisomers (I-A) and (I-A') on the one hand and the stereoisomers (I-B) and (I-B') on the other are in each case enantiomeric to one another. In other respects the stereoisomers are diastereoisomeric among one another. Stereoisomer (I-A) is accordingly preferably enantiomeric to (I-A') and diastereoisomeric to (I-B) and (I-B'), stereoisomer (I-A') is enantiomeric to (I-A) and diastereoisomeric to (I-B) and (I-B'), stereoisomer (I-B) is diastereomeric to (I-A) and (I-A') and enantiomeric to (I-B'), and finally stereoisomer (I-B') is diastereoisomeric to (I-A) and (I-A') and enantiomeric to (I-B).

If, for example, in step (a) of the method of the invention the mixture ratio of the stereoisomers in the mixture is manipulated in such a way that the stereoisomer of the general formula (I-A') is present in an enantiomeric excess, the excess relates to the relative amount of its enantiomer, i.e. preferably to the stereoisomer of the general formula (I-A). The mixture ratio of the optionally likewise present stereoisomers, for example of the general formulae (I-B) and (I-B') need not necessarily be manipulated, such that these may also (optionally still) be present, for example, in the racemic mixture.

In a preferred embodiment of the method of the invention, this serves to isolate one stereoisomer from a mixture comprising the two stereoisomers of the general formulae (I-A) and (I-A'), but not, however, the two stereoisomers of the general formulae (I-B) and (I-B'). In another preferred embodiment of the method of the invention, this serves to isolate one stereoisomer, preferably of the general formula (I-A) or (I-A'), from a mixture of all four stereoisomers, i.e. the stereoisomers of the general formulae (I-A), (I-A'), (I-B) and (I-B').

In a preferred embodiment of the method of the invention, the manipulation in step (a) is carried out
  by addition of the stereoisomer which is to be present in excess, or
  by enantioselective synthesis of the stereoisomers.

The manipulation in step (a) has the consequence that at least one of the stereoisomers is present in an enantiomeric excess. This means preferably that it is relatively enriched in relation to its enantiomer. This enrichment can be achieved in different ways. On the one hand, it involves achieving an enantiomeric excess during the course of synthesis of the stereoisomers, on the other it also involves shifting the relative weight ratio of the two enantiomers of a mixture originally present as a racemate in respect of these two stereoisomers/enantiomers. The latter variant can be achieved, for example, by external addition or enantioselective derivatisation of one of the two enantiomers (e.g. kinetic racemate separation).

If the manipulation in step (a) is carried out by addition of the stereoisomer which is to be present in enantiomeric excess, it can be isolated previously by separate isolation from a mixture of the stereoisomers. For example, it is possible to this end initially to separate the diastereoisomers by selective precipitation of the one enantiomeric pair as hydrochlorides. In this way, the two stereoisomers of the general formula (I-A) and (I-A') (enantiomeric pair 1) may be separated from the two stereoisomers of the general formula (I-B) and I-B') (enantiomeric pair 2). The separation of the two enantiomers, i.e. the separation of the racemic enantiomeric pairs 1 and 2, respectively, can then be carried out with the aid of chiral auxiliaries, for example, chiral acids.

It has now surprisingly been found that the two enantiomers of the general formulae (I-A) and (I-A') may be selectively precipitated with the aid of (+)- and (−)-di-O,O'-p-toluyltartaric acid, the respective other enantiomer remaining in the mother liquor.

One aspect of the invention thus concerns a method for racemate separation of the two enantiomers of the general formulae (I-A) and (I-A') comprising the addition of (+)- or (−)-di-O,O'-p-toluyltartaric acid. A suitable solvent is, for example, 2-butanone. The two enantiomers of the general formulae (I-A) and (I-A') are dissolved in the solvent. Depending upon the configuration of the tartaric acid derivative used, a stereoselective precipitation of the enantiomer of the general formula (I-A) or (I-A') as addition salt takes place after its addition Owing to the comparatively high cost of the enantiomerically pure tartaric acid derivative ((−)- or (+)-di-O,O'-p-toluyltartaric acid) as a chiral auxiliary, this method is only of limited use for enantiomeric separation on a preparative scale. This method is preferably merely used initially to obtain the respective enantiomerically pure stereoisomers of the general formula (I-A) and (I-A') and, through their addition to the reaction mixture, to manipulate the relative weight ratio in favour of one or the other stereoisomer for the purposes of step (a) of the method of the invention, i.e. to produce an enantiomeric excess.

Alternatively, a small but sufficient amount of the enantiomerically pure compounds can be obtained by HPLC on a chiral stationary phase.

In principle, it is also conceivable for the manipulation in step (a) of the method of the invention not to take place by the addition of one enantiomer, but instead by selective removal of the other enantiomer. Thus, for example, alternatively to enrichment of one of the two enantiomers, one of the two enantiomers may be selectively degraded. In this connection, it is for example conceivable to carry out selective enzymatic derivatisation of one stereoisomer, as a result of which its enantiomer is present in excess.

The manipulation in step (a) of the method of the invention can also be carried out by enantioselective synthesis of the stereoisomers. In this case, enantioselectivity can be induced at different steps of the synthesis. Thus it is, for example, possible to induce an excess of one of the two resulting enantiomers by suitable measures even at the stage of the aforementioned Mannich reaction. Suitable measures are known to a person skilled in the art. Alternatively, it is also possible, for example, to induce an enantiomeric excess by enantioselective reaction control in the also previously described Grignard reaction (or an equivalent reaction with another organometallic reagent) subsequent to the Mannich reaction. Suitable methods are known to a person skilled in the art here too. Ojima, Catalytic Asymmetric Synthesis, 2nd ed., Wiley VCH; R. A. Aitken et al., Asymmetric Synthesis, 2nd ed., CRC Press; L. A. Paquette, Handbook of Reagents for Organic Synthesis: Chiral Reagents for Asymmetric Synthesis, John Wiley & Sons; H. B. Kagan, Asymmetric Synthesis, Thieme Medical Pub.; W. Carruthers, Modern Methods of Organic Synthesis, 4th ed., Cambridge University Press; and R. S. Atkinson, Stereoselective Synthesis, John Wiley & Sons.

In a preferred embodiment, the enantiomeric excess after carrying out step (a) of the method of the invention is at least 1.0% ee, more preferably at least 2.5% ee, still more preferably at least 5.0% ee, most preferably at least 7.5% ee and in particular at least 10% ee. However, the enantiomeric excess is preferably at most 25% ee, more preferably at most 20% ee and in particular at most 15% ee.

The enantiomeric excess is defined as $$\frac{[(+)] - [(-)]}{[(+)] + [(-)]} 100\%$$

or $$\frac{[(-)] - [(+)]}{[(+)] + [(-)]} 100\%,$$

[(+)] and [(−)] denoting the concentration of the dextrorotatory and levorotatory enantiomer and a positive number always being obtained.

Suitable methods for the determination of the enantiomeric excess are familiar to a person skilled in the art. HPLC on chiral stationary bases and NMR investigations with chiral shift reagents may be mentioned by way of example.

The method of the invention is successful with N,N-dialkylamino-2-alkyl-3-hydroxy-3-phenylalkanes of different structure.

In a preferred embodiment $R_1$ and $R_3$ are —H. Preferred substitution patterns of the phenyl ring ($R_1$, $R_2$ and $R_3$) are summarized in the following table:

| $R_1$ | $R_2$ | $R_3$ |
|---|---|---|
| —H | —OCH$_3$ | —H |
| —H | —OH | —H |
| —H | —OCH(CH$_3$)$_2$ | —H |
| —H | —OCH$_2$C$_6$H$_5$ | —H |
| —H | —CH$_3$ | —H |
| —H | —CHF$_2$ | —H |
| —H | —CF$_3$ | —H |
| —H | —H | —CF$_3$ |

| $R_1$ | $R_2$ | $R_3$ |
|---|---|---|
| —H | —Cl | —H |
| —H | —F | —H |
| —H | —Cl | —Cl |
| —H | —SCH$_3$ | —H |

$R_1$ and $R_3$ are particularly preferably in each case —H and $R_2$ is —O—$C_1$-$C_6$-alkyl, preferably —OCH$_3$, or —OH. $R_4$ is preferably —$C_1$-$C_6$-alkyl, preferentially —CH$_3$ or —CH$_2$CH$_3$. $R_5$ is preferably —$C_1$-$C_6$-alkyl, preferentially —CH$_3$. $R_6$ and $R_7$ are preferably in each case —$C_1$-$C_6$-alkyl, preferentially —CH$_3$. $R_4$ is particularly preferably —CH$_2$CH$_3$ and $R_5$, $R_6$ and $R_7$ are in each case —CH$_3$.

"$C_1$-$C_6$-alkylene" for the purposes of the description means a linear or branched, cyclic or open-chain saturated hydrocarbon residue with 1 to 6 carbon atoms, optionally substituted with 1 to 6 halogen atoms (identical or different, selected from F, Cl and Br). Examples are —CH$_3$, —CF$_3$, —CH$_2$F, —CHF$_2$, —CH$_2$CH$_3$, —CH(CH$_3$)$_2$, —CH$_2$CH$_2$CH$_3$, —CH(CH$_3$)CH$_2$CH$_3$, —CH$_2$CH(CH$_3$)CH$_3$, —C(CH$_3$)$_3$, —CH$_2$CH$_2$CH$_2$CH$_3$, etc.

"$C_1$-$C_6$-alkylene" for the purposes of the description means a linear or branched, cyclic or open-chain saturated hydrocarbon residue with 1 to 6 carbon atoms, optionally substituted with 1 to 6 halogen atoms (identical or different, selected from F, Cl and Br). Examples are —CH$_2$—, —CH$_2$CH$_2$—, —CH(CH$_3$)CH$_2$—, —CH$_2$CH$_2$CH$_2$—, —CH(CH$_3$)CH$_2$CH$_2$—, —CH$_2$CH(CH$_3$)CH$_2$—, —C(CH$_3$)$_2$CH$_2$—, —CH(CH$_3$)CH(CH$_3$)—, —CH$_2$CH$_2$CH$_2$CH$_2$—, etc.

In one particularly preferred embodiment of the method of the invention $R_1$ is —H, $R_2$—OCH$_3$, $R_3$—H, $R_4$—CH$_2$CH$_3$, $R_5$—CH$_3$, $R_6$—CH$_3$ and $R_7$—CH$_3$, such that the stereoisomers of the general formulae (I-A), (I-A'), (1-B) and (1-B') are 1-dimethyl-amino-3-(3-methoxyphenyl)-2-methylpentan-3-ol.

In this instance, the stereoisomer of the general formula (I-A) is (2S,3S)-1-dimethyl-amino-3-(3-methoxyphenyl)-2-methylpentan-3-ol, the stereoisomer of the general formula (I-A') is (2R,3R)-1-dimethylamino-3-(3-methoxyphenyl)-2-methylpentan-3-ol, the stereoisomer of the general formula (I-B) is (2S,3R)-1-dimethylamino-3-(3-methoxyphenyl)-2-methylpentan-3-ol, and the stereoisomer of the general formula (I-B') is (2R,3S)-1-dimethylamino-3-(3-methoxyphenyl)-2-methylpentan-3-ol, or their salts with organic or inorganic acids.

In a preferred embodiment, the method of the invention comprises the step (b$_1$) addition of a chiral compound of the general formula (II) or (II')

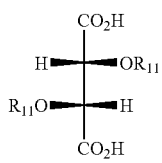

(II)

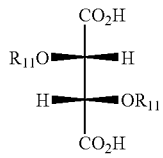

(II')

in which $R_{11}$ is —H, —CO—$C_1$-$C_6$-alkyl, —CO-phenyl or —CO-tolyl.

The chiral compound of the general formula (II) or (II') is preferably added in optically pure form. Its enantiomeric excess is preferably at least 90% ee, more preferably at least 95% ee, most preferably 98% ee and in particular at least 99% ee.

The chiral compounds of the general formula (II) or (II') are tartaric acid or its derivatives. The configuration of the two chiral centres is either R,R or S,S. Tartaric acid and many of its derivatives are available commercially in enantiomerically pure form.

$R_{11}$ is preferably —H or —CO-p-tolyl.

In another preferred embodiment, the method of the invention comprises the step (b$_2$) addition of phosphoric acid.

The addition of phosphoric acid preferably serves to convert at least one of the stereoisomers into the phosphate, hydrogenphosphate or dihydrogenphosphate and consequently to induce selective crystallisation. By means of the stoichiometric ratio between the amount of phosphoric acid added and the stereoisomers of the general formulae (I-A), (I-A'), (I-B) and (I-B') it is possible to exert an influence upon whether salt formation takes place as phosphate ($PO_4^{3-}$), hydrogenphosphate ($HPO_4^{2-}$) or dihydrogenphosphate ($H_2PO_4^{-}$).

Besides the addition of a suitable amount of phosphoric acid, the stereoisomers can be converted into the phosphate, hydrogenphosphate or dihydrogenphosphate in other ways. Such variants are known to a person skilled in the art, for example the addition of phosphate salts and subsequent acidification with mineral acids.

Step (b$_1$) or (b$_2$) is preferably carried out under conditions that bring about the precipitation from a solution of the stereoisomer present in enantiomeric excess as salt of the chiral compound of the general formula (II) or (II'), or as phosphate, hydrogenphosphate or dihydrogenphosphate.

If $R_{11}$ is —H, the chiral compound of the general formula (II) or (II') is tartaric acid. It has surprisingly been found that the stereoisomers of the general formulae (I-A) and (I-A') can in each case be precipitated selectively in step (b$_1$) with one of the two tartaric acid enantiomers if care is first taken to ensure that the two enantiomers of the general formulae (I-A) and (I-A') are not present as a racemate, but instead one of the two enantiomers is present in excess.

It has surprisingly been found that the enantiomeric purity of the precipitate is sometimes significantly greater than the enantiomeric excess before precipitation. The difference between the possibly somewhat low enantiomeric excess before precipitation and the enantiomeric purity of the precipitate can in some cases be quite considerable. Such crystallisation behaviour is unusual and represents a significant advantage of the method of the invention relative to conventional methods for racemate separation.

By using the correct tartaric acid enantiomer it is possible to ensure that practically only the stereoisomer of the general formula (I-A) or (I-A') present in excess is precipitated, while the other enantiomer remains in the stock solution. The suitable enantiomer for the particular situation can be determined by simple preliminary investigations. Owing to the comparatively low costs of the two enantiomers of tartaric acid, this preferred embodiment of the method of the invention is also suitable for use on a preparative scale.

Unlike with tartaric acid or its derivatives of the general formula (II) or (II'), in the case of addition of phosphoric acid in step ($b_2$) no further chiral reagent is added. Instead, the separation of the stereoisomers is based preferentially on the different crystallisation behaviour of the phosphates, hydrogenphosphates or dihydrogenphosphates of the stereoisomers as such. It has surprisingly been found that one enantiomer can be selectively precipitated as phosphate, hydrogenphosphate or dihydrogenphosphate from a mixture of the two enantiomers of the general formulae (I-A) and (I-A') if care has been previously taken to ensure that it is present in a specific, but not necessarily particularly large, enantiomeric excess.

This embodiment of the method of the invention is even suitable for the selective crystallization of one of the stereoisomers from the mixture of all four stereoisomers of the general formulae (I-A), (I-A'), (I-B) and (I-B'). It is accordingly not even necessary initially to carry out a diastereomeric separation, for example by precipitation of one enantiomeric pair as hydrochloride. Instead, selective precipitation is even successful from the immediate reaction product from the Grignard reaction. Ethanol, for example, is a suitable solvent for this purpose.

The method of the invention has the advantage that in step (a) only a comparatively small enantiomeric excess of the stereoisomer need be brought about in order to achieve a high enantiomeric excess of the precipitate during the precipitation with a compound of the general formula (II) or (II') or as phosphate, hydrogenphosphate or dihydrogenphosphate. If, for example, step (a) of the method of the invention is carried out with enantioselective reaction control, the enantioselectivity of the reaction accordingly need not lie in the region of 95% ee and above as is normally required. Instead, even significantly less pronounced enantioselectivities suffice in the synthesis in order ultimately to obtain a product with very high enantiomeric purity.

The method of the invention preferably comprises the step
(c) separation of the precipitated salt obtained in step ($b_1$) or ($b_2$) from the supernatant solution.

This can be achieved, for example, by decantation, filtration, centrifugation, etc.

In a preferred embodiment, the method of the invention comprises the step
(d) conversion of the salt separated in step (c) into the hydrochloride.

Conversion of the separated salt into the hydrochloride can be achieved in different ways. In a preferred embodiment, the separated salt is first converted into the free base of the stereoisomer. This can be carried out by the addition of strong bases, for example NaOH or KOH.

The free base of the stereoisomer released in this way may then either be initially isolated or converted directly into the hydrochloride in situ. It has surprisingly been found that improved yields are obtained during hydrochloride precipitation if hydrogen chloride is used in gaseous form in place of trimethylchlorosilane/water (cf. EP-A 693 475). Suitable solvents are, for example, acetone or 2-butanone.

A further aspect of the invention concerns an addition salt of a stereoisomer of the general formula (I-A), (I-A'), (I-B) or (I-B') as defined above and
  a compound of the general formula (II) or (II') as defined above, or
  phosphoric acid.

The addition salt is preferably selected from the group consisting of
(2R,3R)-1-dimethylamino-3-(3-methoxyphenyl)-2-methyl-pentan-3-ol (+)-tartrate,
(2R,3R)-1-dimethylamino-3-(3-methoxyphenyl)-2-methyl-pentan-3-ol (−)-tartrate,
(2R,3R)-1-dimethylamino-3-(3-methoxyphenyl)-2-methyl-pentan-3-ol (+)-di-O,O'-p-toluyltartrate,
(2R,3R)-1-dimethylamino-3-(3-methoxyphenyl)-2-methyl-pentan-3-ol (−)-di-O,O'-p-toluyltartrate,
(2R,3R)-1-dimethylamino-3-(3-methoxyphenyl)-2-methyl-pentan-3-ol phosphate,
(2R,3R)-1-dimethylamino-3-(3-methoxyphenyl)-2-methyl-pentan-3-ol hydrogenphosphate,
(2R,3R)-1-dimethylamino-3-(3-methoxyphenyl)-2-methyl-pentan-3-ol dihydrogenphosphate,
(2S,3S)-1-dimethylamino-3-(3-methoxyphenyl)-2-methyl-pentan-3-ol (+)-tartrate,
(2S,3S)-1-dimethylamino-3-(3-methoxyphenyl)-2-methyl-pentan-3-ol (−)-tartrate,
(2S,3S)-1-dimethylamino-3-(3-methoxyphenyl)-2-methyl-pentan-3-ol (+)-di-O,O'-p-toluyltartrate,
(2S,3S)-1-dimethylamino-3-(3-methoxyphenyl)-2-methyl-pentan-3-ol (−)-di-O,O'-p-toluyltartrate,
(2S,3S)-1-dimethylamino-3-(3-methoxyphenyl)-2-methyl-pentan-3-ol phosphate,
(2S,3S)-1-dimethylamino-3-(3-methoxyphenyl)-2-methyl-pentan-3-ol hydrogenphosphate,
(2S,3S)-1-dimethylamino-3-(3-methoxyphenyl)-2-methyl-pentan-3-ol dihydrogenphosphate,
(2R,3S)-1-dimethylamino-3-(3-methoxyphenyl)-2-methyl-pentan-3-ol (+)-tartrate,
(2R,3S)-1-dimethylamino-3-(3-methoxyphenyl)-2-methyl-pentan-3-ol (−)-tartrate,
(2R,3S)-1-dimethylamino-3-(3-methoxyphenyl)-2-methyl-pentan-3-ol (+)-di-O,O'-p-toluyltartrate,
(2R,3S)-1-dimethylamino-3-(3-methoxyphenyl)-2-methyl-pentan-3-ol (−)-di-O,O'-p-toluyltartrate,
(2R,3S)-1-dimethylamino-3-(3-methoxyphenyl)-2-methyl-pentan-3-ol phosphate,
(2R,3S)-1-dimethylamino-3-(3-methoxyphenyl)-2-methyl-pentan-3-ol hydrogenphosphate,
(2R,3S)-1-dimethylamino-3-(3-methoxyphenyl)-2-methyl-pentan-3-ol dihydrogenphosphate,
(2S,3R)-1-dimethylamino-3-(3-methoxyphenyl)-2-methyl-pentan-3-ol (+)-tartrate,
(2S,3R)-1-dimethylamino-3-(3-methoxyphenyl)-2-methyl-pentan-3-ol (−)-tartrate,
(2S,3R)-1-dimethylamino-3-(3-methoxyphenyl)-2-methyl-pentan-3-ol (+)-di-O,O'-p-toluyltartrate,
(2S,3R)-1-dimethylamino-3-(3-methoxyphenyl)-2-methyl-pentan-3-ol (−)-di-O,O'-p-toluyltartrate,
(2S,3R)-1-dimethylamino-3-(3-methoxyphenyl)-2-methyl-pentan-3-ol phosphate,
(2S,3R)-1-dimethylamino-3-(3-methoxyphenyl)-2-methyl-pentan-3-ol hydrogenphosphate and
(2S,3R)-1-dimethylamino-3-(3-methoxyphenyl)-2-methyl-pentan-3-ol dihydrogenphosphate.

In a preferred embodiment, the addition salt is selected from the above list, "(3-methoxyphenyl)" in each case being replaced by "(3-hydroxyphenyl)".

A further aspect of the invention concerns a method for the preparation of a stereoisomer of the general formulae (I-A), (I-A'), (I-B) and (I-B') as defined above (preparation method) comprising the method for the isolation of the stereoisomer described above (separation method). The production method preferably comprises a method for the preparation of a stereoisomer of the general formula (I-A), (I-A'), (I-B) or (I-B')

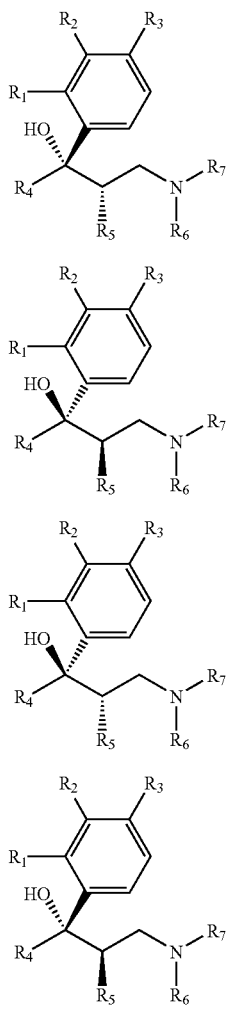

in which $R_1$, $R_2$ and $R_3$, identical or different, are selected from the group consisting of —H, —F, —Cl, —$C_1$-$C_6$-alkyl, —S—$C_1$-$C_6$-alkyl and —OH, providing that at least one of the residues $R_1$, $R_2$ and $R_3$ is —OH;

$R_4$ is —H or —$C_1$-$C_6$-alkyl;

$R_5$ is —$C_1$-$C_6$-alkyl; and $R_6$ and $R_7$, identical or different, are —H or —$C_1$-$C_6$-alkyl;

or their salts with organic or inorganic acids;

comprising the separation method described above for the isolation of a stereoisomer, wherein during the implementation of the separation method at least one of the residues $R_1$, $R_2$ and $R_3$ is —O—$C_1$-$C_6$-alkyl, —O—$C_1$-$C_6$-alkylenephenyl, —OCO—$C_1$-$C_6$-alkyl, —$OCO_2$—$C_1$-$C_6$-alkyl, —OCON($C_1$-$C_6$-alkyl)$_2$ or —O—$SiR_8R_9R_{10}$.

In a preferred embodiment, after isolation of the stereoisomers, i.e. after the implementation of the separation method of the invention, the preparation method of the invention comprises the step (e) conversion of at least one of the residues $R_1$, $R_2$ and $R_3$ which is —O—$C_1$-$C_6$-alkyl, —O—$C_1$-$C_6$-alkylenephenyl, —OCO—$C_1$-$C_6$-alkyl, —$OCO_2$—$C_1$-$C_6$-alkyl, —OCON($C_1$-$C_6$-alkyl)$_2$ or —O—$SiR_8R_9R_{10}$ into an —OH group.

Conversion into an —OH group can be carried out in a manner known to a person skilled in the art, for example with acid, base, fluoride, complex metal hydrides, etc., depending upon the nature of the substitution.

The following examples serve to illustrate the invention but should not be construed to limit the scope thereof.

EXAMPLE 1

Preparation of a Mixture of the Four Stereoisomers of 1-dimethylamino-3-(3-methoxyphenyl)-2-methyl-pentan-3-ol A mixture of the four stereoisomers of 1-dimethylamino-3-(3-methoxyphenyl)-2-methylpentan-3-ol was prepared by a Grignard reaction of rac.-1-dimethylamino-2-methylpentan-3-one with 3-methoxyphenylmagnesium bromide in THF in accordance with example 1 of EP 0 693 475 A1.

The two enantiomers (2R,3R)- and (2S,3S)-1-dimethylamino-3-(3-methoxyphenyl)-2-methylpentan-3-ol and the two enantiomers (2R,3S)- and (2S,3R)-1-dimethylamino-3-(3-methoxyphenyl)-2-methylpentan-3-ol were in each case present in equal amounts, i.e. as a racemate. The ratio of the diastereoisomers (2R,3R)/(2S,RS) to (2R,3S)/(2S,3R) was 70 wt. % to 30 wt. %.

EXAMPLE 2

Diastereoisomer Separation [Separation of the Enantiomeric Pair of (2R,3R)/(2S,3S) Configuration From the Enantiomeric Pair of (2R,3S)/(2S,3R) Configuration]

a) HCl Precipitation

A 100 l double wall jacketed reaction vessel with electric impeller stirrer, gas transfer line, Pt100 temperature sensor and oil-based cooling and heating system was charged with 15 kg (59.7 mol) of a mixture of the enantiomeric pair (2R, 3R)/(2S,3S)-1-dimethylamino-3-(3-methoxyphenyl)-2-methylpentan-3-ol (70%) and the enantiomeric pair (2R,3S)/(2S,3R)-1-dimethylamino-3-(3-methoxyphenyl)-2-methylpentan-3-ol (30%) in 70 l of acetone at 20° C. and a stirrer speed of 100 rpm The solution was cooled to 5° C. Within 20 min, approx. 2.0 kg of gaseous hydrogen chloride were passed over the solution, the temperature in the vessel rising continuously to 28° C. despite cooling. The hydrogen chloride was taken from a hydrogen chloride cylinder which was connected to the gas transfer line of the vessel through a pressure reduction valve and hose and was placed on a balance for weight measurement. Further gaseous hydrogen chloride was then passed over until a 5 ml sample of the solution diluted with 10 ml of water had a pH value of 1-3. The solution was stirred at 5° C. for 2 h. The suspension was then centrifuged off in a centrifuge and washed once with 10 l of acetone. The product was dried in a drying cabinet at 40° C. for 24 h under reduced pressure to a final pressure of 20 mbar. 11.16 kg (65% of theoretical) of the enantiomeric pair (2R,3R)/(2S,3S)-1-dimethylamino-3-(3-methoxyphenyl)-2-methylpentan-3-ol hydrochloride were obtained as a colourless product. The residual content of the undesired enantiomeric pair (2S,3R)/(2R,3S)-1-dimethylamino-3-(3-methoxyphenyl)-2-methylpentan-3-ol hydrochloride was 3%.

b) Conversion of the Hydrochloride into the Free Base

A 100 l double wall jacketed reaction vessel with electric impeller stirrer, Pt100 temperature sensor and oil-based cooling and heating system was charged with 11.16 kg (38, 78 mol) of the enantiomeric pair (2R,3R)/(2S,3S)-1-dimethylamino-3-(3-methoxyphenyl)-2-methylpentan-3-ol hydrochloride from step a), contaminated with 3% of the enantiomeric pair (2R,3S)/(2S,3R)-1-dimethylamino-3-(3-methoxyphenyl)-2-methylpentan-3-ol hydrochloride in 21 l of water at 20° C. The solution was treated with 32 wt. % aqueous sodium hydroxide solution up to a pH value of 13 and then extracted with 21 l of ethyl acetate. After evaporation of the ethyl acetate at 60-65° C. to a final vacuum of 20 mbar, the base remained as a colourless oil with a yield of 8.77 kg (90% of theoretical), contaminated with 3% of the enantiomeric pair (2S,3R)/(2R,3S)-1-dimethylamino-3-(3-methoxyphenyl)-2-methylpentan-3-ol.

c) Recrystallisation as Hydrochloride

A 100 l double wall jacketed reaction vessel with electric impeller stirrer, gas transfer line, Pt100 temperature sensor and oil-based cooling and heating system was charged with 15 kg (59.7 mol) of a mixture of the enantiomeric pair (2R,3R)/(2S,3S)-1-dimethylamino-3-(3-methoxyphenyl)-2-methylpentan-3-ol (97%) and the enantiomeric pair (2R,3S)/(2S,3R)-1-dimethylamino-3-(3-methoxyphenyl)-2-methylpentan-3-ol (3%) in 70 l of acetone at 20° C. at a stirrer speed of 100 rpm. The solution was cooled to 5° C. Within 20 min, approx. 2.0 kg of gaseous hydrogen chloride were passed over the solution, the temperature in the vessel rising continuously to 28° C. despite cooling. The hydrogen chloride was taken from a hydrogen chloride cylinder which was connected to the gas transfer line of the vessel through a pressure reduction valve and hose and was placed on a balance for weight measurement. Further gaseous hydrogen chloride was then passed over until a 5 ml sample of the solution diluted with 10 ml of water had a pH value of 1-3. The solution was stirred at 5° C. for 2 h. The suspension was then centrifuged off in a centrifuge and washed once with 10 l of acetone. The product was dried in a drying cabinet at 40° C. for 24 h under reduced pressure to a final pressure of 20 mbar. 13.74 kg (80% of theoretical) of the colourless enantiomeric pair (2R,3R)/(2S,3S)-1-dimethylamino-3-(3-methoxyphenyl)-2-methylpentan-3-ol hydrochloride with a diastereomeric purity of 100% were obtained.

d) Conversion of the Hydrochloride into the Free Base

A 100 l double wall jacketed reaction vessel with electric impeller stirrer, Pt100 temperature sensor and oil-based cooling and heating system was charged with 13.74 kg (47.7 mol) of the enantiomeric pair (2R,3R)/(2S,3S)-1-dimethylamino-3-(3-methoxyphenyl)-2-methylpentan-3-ol hydrochloride in 26 l of water at 20° C. The solution was treated with 32 wt. % aqueous sodium hydroxide solution up to a pH value of 13 and then extracted with 26 l of ethyl acetate. After evaporation of the ethyl acetate at 60-65° C. to a final vacuum of 20 mbar, the enantiomeric pair (2R,3R)/(2S,3S)-1-dimethylamino-3-(3-methoxyphenyl)-2-methylpentan-3-ol remained as colourless oil with a yield of 10.80 kg (90% of theoretical) and a diastereomeric purity of 100%.

EXAMPLE 3

Separation of the Two Enantiomers of (2R,3R) and (2S,3S) Configuration with the Aid of (+)-di-O,O'-p-toluyltartaric Acid a) Precipitation of (2S,3S)-1-dimethylamino-3-(3-methoxyphenyl)-2-methylpentan-3-ol; (+)-di-O,O'-p-toluyltartrate A 2 l three-necked flask with thermometer, mechanical pneumatic stirrer, reflux condenser and oil bath heating was charged with 121 g (0.48 mol) of the enantiomeric pair (2R,3R)/(2S,3S)-1-dimethylamino-3-(3-methoxyphenyl)-2-methylpentan-3-ol (with a diastereomeric purity of 100%) in 100 ml of 2-butanone and a solution of 185.6 g (0.48 mol) of (+)-di-O,O'-p-toluyltartaric acid dissolved in 1700 ml of 2-butanone was added with stirring. After 48 h at room temperature, the resulting crystal mass was filtered off through a vacuum filter under reduced pressure and washed twice with 150 ml of cooled (3-8° C.) 2-butanone each time. The product was dried in a drying cabinet at 40° C. for 24 h to a final vacuum of 20 mbar. 125 g (40% of theoretical) of (2S,3S)-1-dimethylamino-3-(3-methoxyphenyl)-2-methylpentan-3-ol (+)-di-O,O'-p-toluyltartrate were obtained which were used without further purification for release of the base.

b) Conversion of the (+)-di-O,O'-p-toluyltartrate into the Free Base 125 g (0.2 mol) of (2S,3S)-1-dimethylamino-3-(3-methoxyphenyl)-2-methylpentan-3-ol (+)-di-O,O'-p-toluyltartrate were dissolved in 500 ml of water, treated with stirring with 18 ml of 37 wt. % hydrochloric acid and extracted twice with 150 ml of diethyl ether each time. The aqueous phase was then treated with 35 ml of 32 wt. % aqueous sodium hydroxide solution and then extracted with 2×250 ml of dichloromethane. After distilling off the solvent at 40° C. to a final pressure of 20 mbar, 47 g (95% of theoretical) of a colourless oil were obtained which consisted of 83% (2S,3S)-1-dimethylamino-3-(3-methoxyphenyl)-2-methylpentan-3-ol and 17% (2R,3R)-1-dimethylamino-3-(3-methoxyphenyl)-2-methylpentan-3-ol.

c) Isolation of the Other Enantiomer from the Mother Liquor as Hydrochloride and Conversion into the Free Base The mother liquor from the precipitation in step a) was combined with both washings, treated with 820 ml of water and 30 ml of 37 wt. % hydrochloric acid were added with stirring. The aqueous phase was extracted twice with 250 ml of diethyl ether each time. To release the base, the aqueous phase was treated with 57 ml of 32 wt. % aqueous sodium hydroxide solution and then extracted with 2×250 ml of dichloromethane. After distilling off the solvent at 40° C. to a final pressure of 20 mbar, 70 g (58% of theoretical) of a colourless oil were obtained which consisted of 70% (2R,3R)-1-dimethylamino-3-(3-methoxyphenyl)-2-methylpentan-3-ol and 30% (2S,3S)-1-dimethylamino-3-(3-methoxyphenyl)-2-methylpentan-3-ol.

EXAMPLE 4

Separation of the Two Enantiomers of (2R,3R) and (2S,3S) Configuration with the Aid of (−)-di-O,O'-p-toluyltartaric Acid a) Precipitation of (2R,3R)-1-dimethylamino-3-(3-methoxyphenyl)-2-methylpentan-3-ol (−)-di-O,O'-p-toluyltartrate 13.7 g (54.5 mmol) of the enantiomeric pair (2R,3R)/(2S,3S)-1-dimethylamino-3-(3-methoxyphenyl)-2-methylpentan-3-ol (with a diastereomeric purity of 100%) and 10 ml of 2-butanone were treated with stirring with a solution of 22 g (56.9 mmol) of (−)-di-O,O'-p-toluyltartaric acid in 220 ml of 2-butanone. After 24 h at room temperature, the resulting crystal mass was filtered through a vacuum filter under reduced pressure and washed twice with 15 ml of cooled (3-8° C.) 2-butanone each time. The product was dried for 24 h in a drying cabinet at a temperature of 40° C. and a final vacuum of 20 mbar. 8.7 g (25% of theoretical) of (2R,3R)-1-dimethylamino-3-(3-methoxyphenyl)-2-methylpentan-3-ol (−)-di-O, O'-p-toluyltartrate were obtained which were used without further purification for release of the base.

b) Conversion of the (−)-di-O,O'-p-toluyltartrate into the Free Base 8.7 g (13.6 mmol) of (2R,3R)-1-dimethylamino-3-(3-methoxyphenyl)-2-methylpentan-3-ol (−)-di-O,O'-p-toluyltartrate were dissolved in 30 ml of water in a 100 ml three-necked flask with thermometer, magnetic stirrer and reflux condenser, treated with stirring with 1.1 ml of 37 wt. % hydrochloric acid and extracted twice with 15 ml of diethyl ether each time. 2.2 ml of 32 wt. % aqueous sodium hydroxide solution were then added to the aqueous phase which was then extracted with 2×20 ml of dichloromethane. After distilling off the solvent at 40° C. to a final pressure of 20 mbar, 3.36 g (98% of theoretical) of a colourless oil were obtained which consisted of 65% (2R,3R)-1-dimethylamino-3-(3-methoxyphenyl)-2-methylpentan-3-ol and 35% (2S,3S)-1-dimethylamino-3-(3-methoxyphenyl)-2-methylpentan-3-ol.

EXAMPLE 5

Separation of the Two Enantiomers of (2R,3R) and (2S,3S) Configuration with the Aid of D-(−)-tartaric Acid After Enrichment of the Enantiomer of (2R,3R) Configuration a) Precipitation of (2R,3R)-1-dimethylamino-3-(3-methoxyphenyl)-2-methylpentan-3-ol (−)-tartrate A 2 l three-necked flask with thermometer, mechanical pneumatic stirrer, reflux condenser and oil bath heating was charged with 30 g (0.12 mol) of the mixture of the two enantiomers obtained in Example 4b) with an enantiomeric excess of 30% ee (65 wt. % (2R,3R)-1-dimethylamino-3-(3-methoxyphenyl)-2-methylpentan-3-ol and 35 wt. % (2S,3S)-1-dimethylamino-3-(3-methoxyphenyl)-2-methylpentan-3-ol) in 50 ml of ethanol and a solution of 18.0 g (0.12 mol) of (−)-(2S,3S)-tartaric acid in 200 ml of ethanol was added with stirring. After 1 h at room temperature, 200 ml of diethyl ether were added and stirring was continued for 24 h. The resulting crystal mass was filtered through a vacuum filter under reduced pressure and washed twice with 200 ml of cooled (3-8° C.) diethyl ether each time. The product was dried for 24 h in a drying cabinet at a temperature of 40° C. and a final vacuum of 20 mbar. 26.4 g (55% of theoretical) of (2R,3R)-1-dimethylamino-3-(3-methoxyphenyl)-2-methylpentan-3-ol (−)-tartrate were obtained which were used without further purification for release of the base.

b) Conversion of the (−)-tartrate into the Free Base 26.4 g (65.8 mmol) of (2R,3R)-1-dimethylamino-3-(3-methoxyphenyl)-2-methylpentan-3-ol (−)-tartrate were dissolved in 100 ml of water, treated with stirring with 7.4 ml of 32 wt. % aqueous sodium hydroxide solution and then extracted with 2×50 ml of dichloromethane. After distilling off the solvent at 40° C. to a final pressure of 20 mbar, 16.2 g (98% of theoretical) of a colourless oil were obtained which consisted of 98% (2R,3R)-1-dimethylamino-3-(3-methoxyphenyl)-2-methylpentan-3-ol and 2% (2S,3S)-1-dimethylamino-3-(3-methoxyphenyl)-2-methylpentan-3-ol.

EXAMPLE 6

Separation of the two enantiomers of (2R,3R) and (2S,3S) configuration with the aid of L-(+)-tartaric acid after enrichment of the enantiomer of (2S,3S) configuration a) Precipitation of (2S,3S)-1-dimethylamino-3-(3-methoxyphenyl)-2-methylpentan-3-ol (+)-tartrate A 100 l double wall jacketed reaction vessel with electric impeller stirrer, Pt100 temperature sensor and oil-based cooling and heating system was charged with 6.93 kg (46.17 mol) of (+)-(2R,3R)-tartaric acid in 75 l of ethanol. Then, 10.55 kg (41.97 mol) of a racemic mixture of the enantiomeric pair (2R,3R)/(2S,3S)-1-dimethylamino-3-(3-methoxyphenyl)-2-methylpentan-3-ol in 3.5 l of ethanol were introduced. The racemic mixture was enriched in respect of the enantiomer with the (2S,3S) configuration by addition of 1.06 kg (4.21 mol) of the enantiomerically pure compound (2S,3S)-1-dimethylamino-3-(3-methoxyphenyl)-2-methylpentan-3-ol. This mixture was added to the prepared tartaric acid at 10° C. and stirred at a stirrer speed of 150 rpm for 20 hours. The crystals were centrifuged off and dried in a drying cabinet at 50° C. under reduced pressure for 12 h. After 24 h drying in a drying cabinet at 40° C. and a final pressure of 20 mbar, 8.34 kg (20.77 mol, 45% of theoretical) of (2S,3S)-1-dimethylamino-3-(3-methoxyphenyl)-2-methylpentan-3-ol (+)-tartrate were isolated as colourless crystals which were used as dried or moist with ethanol for release of the base. The other enantiomer (2R,3R)-1-dimethylamino-3-(3-methoxyphenyl)-2-methylpentan-3-ol could be isolated from the centrifugation mother liquor.

b) Conversion of the (+)-tartrate into the Free Base 16.68 kg (41.55 mol) of ethanol-moist or dried (2S,3S)-1-dimethylamino-3-(3-methoxyphenyl)-2-methylpentan-3-ol (+)-tartrate from step a) were dissolved in 65 l of water in a 100 l double wall jacketed reaction vessel with electric impeller stirrer, Pt100 temperature sensor and oil-based cooling and heating system and treated with approx. 5.2 kg of 32 wt. % aqueous sodium hydroxide solution until a pH value of 12-13 was reached. The temperature was kept below 35° C. by cooling the reaction vessel. 30 l of ethyl acetate were added, and after 10 min stirring, the stirrer was switched off to allow phase separation. The lower aqueous phase was drained off and the upper organic phase was distilled at a maximum internal temperature of 50° C. under reduced pressure to 10 mbar. The remaining pale yellow oily residue was (2S,3S)-1-dimethylamino-3-(3-methoxyphenyl)-2-methylpentan-3-ol hydrochloride. The yield was 9.92 kg (95% of theoretical) with an enantiomeric purity of 98.5%.

c) Recrystallisation as Hydrochloride

A 100 l double wall jacketed reaction vessel with electric impeller stirrer, gas transfer line Pt100 temperature sensor and oil-based cooling and heating system was charged with 15 kg (59.7 mol) of a mixture of (2S,3S)-1-dimethylamino-3-(3-methoxyphenyl)-2-methylpentan-3-ol (98%) and (2R,3R)-1-dimethylamino-3-(3-methoxyphenyl)-2-methylpentan-3-ol (2%) in 70 l of acetone at 20° C. and a stirrer speed of 100 rpm. The solution was cooled to 5° C. Within 20 min, approx. 2.0 kg of gaseous hydrogen chloride were passed over the solution, the temperature in the vessel rising continuously to 28° C. despite cooling. The hydrogen chloride was taken from a hydrogen chloride cylinder which was connected to the gas transfer line of the vessel through a pressure reduction valve and hose and was placed on a balance for weight measurement. Further gaseous hydrogen chloride was then passed over until a 5 ml sample of the solution diluted with 10 ml of water had a pH value of 1-3. The suspension was stirred 5° C. for 2 h. The suspension was then centrifuged off in a centrifuge and washed once with 10 l of acetone. The product was dried in a drying cabinet at 40° C. for 24 h under reduced pressure to a final pressure of 20 mbar. 13.74 kg (80% of theoretical) of colourless (2S,3S)-1-dimethylamino-3-(3-methoxyphenyl)-2-methylpentan-3-ol hydrochloride with an enantiomeric purity of 100% were obtained.

d) Isolation of the Other Enantiomer from the Mother Liquor from Step a) as Free Base.

The ethanol of the mother liquor from the centrifugation of the precipitation of (2S,3S)-1-dimethylamino-3-(3-methoxyphenyl)-2-methylpentan-3-ol (+)-tartrate was distilled off in a 100 l double wall jacketed reaction vessel with electric impeller stirrer, Pt100 temperature sensor and oil-based cooling and heating system at an internal temperature of 75° C. and a final pressure of <50 mbar. The residue was dissolved in 22 l of water and treated with 32 wt. % aqueous sodium hydroxide solution until a pH value of 12-13 was reached. The internal temperature was kept below 25° C. by cooling the reaction vessel. 22 l of ethyl acetate were added, stirred for 10 min and the stirrer was switched off to allow phase separation. The lower aqueous phase was drained off and extracted with a further 11 l of ethyl acetate. The two combined ethyl acetate phases were distilled off at a maximum internal temperature of 60° C. under reduced pressure to a final pressure of 10 mbar. The yield of (2R,3R)-1-dimethylamino-3-(3-methoxyphenyl)-2-methylpentan-3-ol was 5.8 kg (50% of theoretical).

EXAMPLE 7

Isolation of the Enriched Enantiomer of (2S,3S) Configuration from the Mixture of all Four Diastereoisomers [Product of the Grignard Reaction in Example 1] with the Aid of L-(+)-tartaric Acid A 100 l double wall jacketed reaction vessel with electric impeller stirrer, Pt100 temperature sensor and oil-based cooling and heating system was charged with 6.93 kg (46.17 mol) of (+)-(2R,3R)-tartaric acid in 75 l of ethanol. Then a mixture of 10.55 kg (41.97 mol) of the enantiomeric pair (2R,3R)/(2S,3S)-1-dimethylamino-3-(3-methoxyphenyl)-2-methylpentan-3-ol (70%) and the enantiomeric pair (2R,3S)/(2S,3R)-1-dimethylamino-3-(3-methoxyphenyl)-2-methylpentan-3-ol (30%) in 3.5 l of ethanol was enriched in respect of the enantiomer with the (2S,3S) configuration by the addition of 1.06 kg (4.21 mol) of the enantiomerically pure (2S,3S)-1-dimethylamino-3-(3-methoxyphenyl)-2-methylpentan-3-ol. This mixture was added to the prepared tartaric acid at 10° C. and stirred at a stirrer speed of 150 rpm for 20 hours. The crystals were centrifuged off and dried in a drying cabinet at 50° C. for 12 h under reduced pressure to a final pressure of 20 mbar. 5.93 kg (32% of theoretical) of colourless crystals of 1-dimethylamino-3-(3-methoxyphenyl)-2-methylpentan-3-ol (+)-tartrate with a composition of the stereoisomers of 98.2% (2S,3S)-1-dimethylamino-3-(3-methoxyphenyl)-2-methylpentan-3-ol (+)-tartrate, 0.8% (2R,3R)-1-dimethylamino-3-(3-methoxyphenyl)-2-methylpentan-3-ol (+)-tartrate and 1% of the enantiomeric pair (2R,3S)/(2S,3R)-1-dimethylamino-3-(3-methoxyphenyl)-2-methylpentan-3-ol (+)-tartrate were obtained.

EXAMPLE 8

Separation of the Two Enantiomers of (2R,3R) and (2S,3S) Configuration with the Aid of Phosphoric Acid Precipitation of the Enantiomer of (2S,3S) Configuration a) With Seeding 10 g (0.04 mol) of the enantiomeric pair (2R,3R)/(2S,3S)-1-dimethylamino-3-(3-methoxyphenyl)-2-methylpentan-3-ol were dissolved in 40 ml of ethanol, treated with stirring with 3 g of 85 wt. % ortho-phosphoric acid and seeded with 1 g (2.86 mmol) of (2S,3S)-1-dimethylamino-3-(3-methoxyphenyl)-2-methylpentan-3-ol phosphate. After 24 h, the crystals formed were filtered off under reduced pressure and dried for 24 h in a drying cabinet at 40° C. to a final pressure of 10 mbar. 3.3 g (22% of theoretical) of (2S,3S)-1-dimethylamino-3-(3-methoxyphenyl)-2-methylpentan-3-ol phosphate were obtained as colourless crystals with an enantiomeric purity of 99.1%.

b) Without Seeding 10 g (0.04 mol) of the enantiomeric pair (2R,3R)/(2S,3S)-1-dimethylamino-3-(3-methoxyphenyl)-2-methylpentan-3-ol were dissolved in 40 ml of ethanol and treated with stirring with 3 g of 85 wt. % ortho-phosphoric acid. After 24 h, the crystals formed were filtered off under reduced pressure and dried for 24 h in a drying cabinet at 40° C. to a final pressure of 10 mbar. 2.2 g (16% of theoretical) of (2S,3S)-1-dimethylamino-3-(3-methoxyphenyl)-2-methylpentan-3-ol phosphate were obtained as colourless crystals with an enantiomeric purity of 85%.

EXAMPLE 9

Separation of the Two Enantiomers of (2R,3R) and (2S,3S) Configuration with the Aid of Phosphoric Acid Precipitation of the Enantiomer of (2R,3R) Configuration from the Mother Liquor of the (+)-tartaric Acid Precipitation of Example 6 a) 1st. Phosphate Precipitation and Base Release

The 7 kg (27.84 mol) of (2R,3R)-1-dimethylamino-3-(3-methoxyphenyl)-2-methylpentan-3-ol from Example 6d) were dissolved in 42 l of ethanol at a temperature of 25° C. in a 100 l double wall jacketed reaction vessel with electric impeller stirrer, Pt100 temperature sensor and oil-based cooling and heating system. 2.16 kg of 85 wt. % ortho-phosphoric acid were added at a stirrer speed of 100 $min^{-1}$ and the solution was cooled to 5° C. After 24 h, the crystals formed were centrifuged off and washed with 7 l of ethanol. The precipitate (phosphate salt) was dissolved in 42 l of water and treated with 32 wt. % aqueous sodium hydroxide solution until a pH value of 12-13 was reached. The temperature was kept below 35° C. by cooling the reaction vessel. 20 l of ethyl acetate were added and, after stirring for 10 min, the stirrer was switched off to allow phase separation. The lower aqueous phase was extracted again with 12 l of ethyl acetate, the organic phases were combined and distilled off at a maximum internal temperature of 50° C. under reduced pressure to 10 mbar. 4.9 kg (70% of theoretical) of a colourless oil were obtained which was used as such in the second phosphate precipitation.

19 b) 2nd Phosphate Precipitation and Base Release 4.9 kg (19.5 mol) of the (2R,3R)-1-dimethylamino-3-(3-methoxyphenyl)-2-methylpentan-3-ol from step a) were dissolved in 30 l of ethanol at a temperature of 25° C. in a 100 l double wall jacketed reaction vessel with electric impeller stirrer, Pt100 temperature sensor and oil-based cooling and heating system. 1.51 kg of 85 wt. % ortho-phosphoric acid were added at a stirrer speed of 100 $min^{-1}$ and the solution was cooled to 5° C. After 24 h, the crystals formed were centrifuged off and washed with 5 l of ethanol. The precipitate was dissolved in 30 l of water and treated with 32 wt. % aqueous sodium hydroxide solution until a pH value of 12-13 was reached. The temperature was kept below 35° C. by cooling the reaction vessel. 14 l of ethyl acetate were added and, after stirring for 10 min, the stirrer was switched off to allow phase separation. The lower aqueous phase was extracted again with 9 l of ethyl acetate, the organic phases were combined and distilled off at a maximum internal temperature of 50° C. under reduced pressure to 10 mbar. 2.5 kg (51% of theoretical) of a colourless oil with an enantiomeric purity of 97% were obtained.

c) Recrystallisation as Hydrochloride

A 100 l double wall jacketed reaction vessel with electric impeller stirrer, gas transfer line, Pt100 temperature sensor and oil-based cooling and heating system was charged with the 10 kg (39.8 mol) of the mixture of (2R,3R)-1-dimethylamino-3-(3-methoxyphenyl)-2-methylpentan-3-ol (97%) and (2S,3S)-1-dimethylamino-3-(3-methoxyphenyl)-2-methylpentan-3-ol (3%) from step b) in 45 l of acetone at 20° C. and a stirrer speed of 100 rpm. The solution was cooled to 5° C. Within 20 min, approx. 1.3 kg of gaseous hydrogen chloride were passed over the solution, the temperature in the vessel rising continuously to 28° C. despite cooling. The hydrogen chloride was taken from a hydrogen chloride cylinder which was connected to the gas transfer line of the vessel through a pressure reduction valve and hose and was placed on a balance for weight measurement. Further gaseous hydrogen chloride was then passed over until a 5 ml sample of the solution diluted with 10 ml of water had a pH value of 1-3. The solution was stirred at 5° C. for 2 h. The suspension was centrifuged off in a centrifuge and washed once with 7 l of acetone. The product was dried in a drying cabinet at 40° C. for 24 h under reduced pressure to a final pressure of 20 mbar. 9.73 kg (85% of theoretical) of colourless (2R,3R)-1-dimethylamino-3-(3-methoxyphenyl)-2-methylpentan-3-ol hydrochloride with an enantiomeric purity of 100% were obtained.

The invention claimed is:

1. A method for isolating a stereoisomer from a mixture comprising the two stereoisomers of formulas I-A and I-A' or the two stereoisomers of formulas I-B and I-B' or all four stereoisomers of formulas I-A, I-A', I-B and I-B'

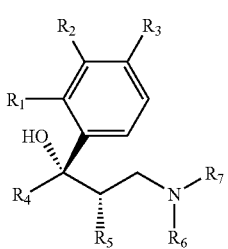

(I-A)

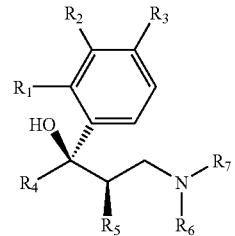

(I-A')

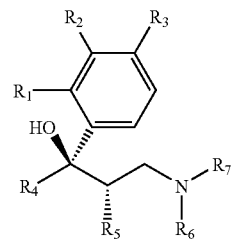

(I-B)

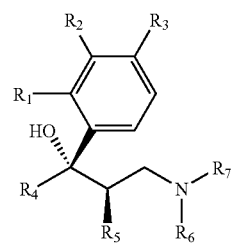

(I-B')

wherein $R_1$, $R_2$ and $R_3$ are each independently selected from the group consisting of —H, —F, —Cl, —$C_1$-$C_6$-alkyl, —S—$C_1$-$C_6$-alkyl, —OH, —O—$C_1$-$C_6$-alkyl, —O—$C_1$-$C_6$-alkylenephenyl, —OCO—$C_1$-$C_6$-alkyl, —$OCO_2$—$C_1$-$C_6$-alkyl, —OCON($C_1$-$C_6$-alkyl)$_2$ and —O—$SiR_8R_9R_{10}$, wherein $R_8$, $R_9$ and $R_{10}$ are each independently selected from the group consisting of —$C_1$-$C_6$-alkyl and -phenyl;

$R_4$ is —H or —$C_1$-$C_6$-alkyl;

$R_5$ is —$C_1$-$C_6$-alkyl; and $R_6$ and $R_7$, are each independently selected from the group consisting of —H and —$C_1$-$C_6$-alkyl;

or salts thereof with organic or inorganic acids;

said method comprising:

(a) manipulating the mixture ratio of the stereoisomers in the mixture so that at least one of the stereoisomers is present in an enantiomeric excess, and (b) adding phosphoric acid under conditions which bring about precipitation of the stereoisomer present in enantiomeric excess from a solution as phosphate, hydrogenphosphate or dihydrogenphosphate.

2. A method according to claim 1, wherein step (a) is carried out by:

adding the stereoisomer which is to be present in excess, or enantioselective synthesis of the stereoisomers.

3. A method according to claim 1, wherein the enantiomeric excess is at least 1.0% ee.

4. A method according to claim 1, wherein $R_1$ and $R_3$ are each —H, and $R_2$ is —$OCH_3$.

5. A method according to claim 1, wherein
R$_4$ is —CH$_2$CH$_3$, and
R$_5$, R$_6$ and R$_7$ are each —CH$_3$.

6. A method according to claim 1, further comprising:
(c) separating the precipitated salt obtained in (b) from a supernatant solution.

7. A method according to claim 6, further comprising:
(d) converting the separated salt obtained in (c) into a hydrochloride salt.

8. A method according to claim 1, wherein at least one of R$_1$, R$_2$ and R$_3$ in the isolated compound is selected from the group consisting of —O—C$_1$-C$_6$-alkyl, —O—C$_1$-C$_6$-alkylenephenyl, —OCO—C$_1$-C$_6$-alkyl, —OCO$_2$—C$_1$-C$_6$-alkyl, —OCON(C$_1$-C$_6$-alkyl)$_2$, and —O—SiR$_8$R$_9$R$_{10}$;
said method further comprising converting the at least one —O—C$_1$-C$_6$-alkyl, —O—C$_1$-C$_6$-alkylenephenyl, —OCO—C$_1$-C$_6$-alkyl, —OCO$_2$—C$_1$-C$_6$-alkyl, —OCON(C$_1$-C$_6$-alkyl)$_2$, and —O—SiR$_8$R$_9$R$_{10}$ group to an —OH group to obtain a compound of formula I-A, I-A', I-B or I-B' in which at least one of R$_1$, R$_2$ and R$_3$ is —OH.

* * * * *